(12) United States Patent
Schnablegger

(10) Patent No.: US 9,329,143 B2
(45) Date of Patent: May 3, 2016

(54) METHOD AND APPARATUS FOR INVESTIGATING THE X-RAY RADIOGRAPHIC PROPERTIES OF SAMPLES

(75) Inventors: Heimo Schnablegger, Graz (AT); Edith Pieber, legal representative, Arnoldstein (AT)

(73) Assignee: Anton Paar GmbH, Graz-Strassgang (AT)

( * ) Notice: Subject to any disclaimer, the term of this patent is extended or adjusted under 35 U.S.C. 154(b) by 123 days.

(21) Appl. No.: 14/004,999

(22) PCT Filed: Mar. 12, 2012

(86) PCT No.: PCT/AT2012/000059
§ 371 (c)(1),
(2), (4) Date: Dec. 18, 2013

(87) PCT Pub. No.: WO2012/122577
PCT Pub. Date: Sep. 20, 2012

(65) Prior Publication Data
US 2014/0098940 A1     Apr. 10, 2014

(30) Foreign Application Priority Data

Mar. 17, 2011 (AT) .................................. A 377/2011

(51) Int. Cl.
*G01N 23/201* (2006.01)
*G01N 23/20* (2006.01)

(52) U.S. Cl.
CPC .......... *G01N 23/20008* (2013.01); *G01N 23/20* (2013.01); *G01N 2223/054* (2013.01); *G01N 2223/3307* (2013.01)

(58) Field of Classification Search
CPC ................. G01N 2223/3307; G01N 2223/054
USPC .......................................................... 378/86
See application file for complete search history.

(56) References Cited

U.S. PATENT DOCUMENTS

2012/0051518 A1* 3/2012 Omote et al. .................... 378/86

* cited by examiner

*Primary Examiner* — Courtney Thomas
(74) *Attorney, Agent, or Firm* — Dennemeyer & Associates, LLC.

(57) ABSTRACT

The invention relates to a method and an apparatus for studying the X-ray properties of samples (3c), wherein X-ray radiation scattered by a sample (3c) is recorded by a detector (5) positioned at a distance from the sample (3c) and is evaluated with respect to the characteristics of the sample. According to the invention, it is provided that at a predetermined distance between the X-ray beam source (1) and the detector (5) or between the starting point (2b) of the X-ray beam (10) directed at the sample (3c) and the detector (5), for a predetermined number of successive measurements the distance (S1, S2) between the sample (3c) and the detector (5) is changed and is set at a predetermined different value.

11 Claims, 3 Drawing Sheets

METHOD AND APPARATUS FOR INVESTIGATING THE X-RAY RADIOGRAPHIC PROPERTIES OF SAMPLES

The invention relates to a method according to the preamble of claim 1, and an apparatus according to the preamble of claim 8.

The invention relates to a method and an apparatus for characterisation of the structure of samples by means of small-angle and large-angle or wide-angle scattering of X-ray radiation.

The elastic scattering of X-ray radiation is used for non-destructive characterisation of the structure of various sample materials.

X-ray scattering occurs when a beam of X-ray radiation impinges on an inhomogeneous, pulverulent, liquid, and/or solid material having a structure in the order of magnitude of the wavelength of the X-ray radiation employed. The X-rays penetrate into the sample, and the material being studied interacts with the X-ray beam, resulting in scattering. This results in characteristic interference images. The form of distribution of the scattered waves is characteristic for the size and symmetry of the scattering particles. Scattering experiments can be carried out with X-ray radiation or similarly with neutron radiation.

In principle, scattering experiments can be carried out in two different geometries: (1) reflection geometry, and (2) transmission geometry. The samples are positioned either at a small incident angle with respect to the measurement beam, the measurement is performed at a grazing incidence close to the critical angle of total reflection and the pattern of the scattered radiation is recorded (GISAXS), or the sample is positioned so as to have the beam transmitted through it. With the first method, information is obtained about the surface structure of the sample, whilst with transmission scattering the nanostructure of the overall penetrated sample volume is analysed (SAXS). As X-ray source, one may use, e.g. an X-ray tube, a rotating anode, or a synchrotron.

Bragg's law provides the basis for interpretation of the X-ray diffraction. The formula is $$n\lambda = 2d \sin\theta,$$

where n is an integer representing the order of the reflection, $\lambda$ is the wavelength, and $\theta$ is one half the scattering angle.

Often in the interpretation the momentum transfer, q, is used, defined as follows:

$$q = \frac{4\pi}{\lambda}\sin(\theta).$$

Typical SAXS measurements are carried out with X-ray wavelengths in the order of 0.1 nm, with evaluation in a scattering-angle range of 0.1-10°. This provides information about the sizes, size distribution, shape, and inner structure of macromolecules, characteristic distances of partially oriented materials, pore sizes, etc., in the range of sizes of 1 to 100 nm. Thus the method covers the range of sizes of numerous technologically interesting nanostructures such as those of biopolymers, liquid crystals, nanoporous materials, microemulsions, nanocomposites, etc.

According to Bragg's law, the smaller the scattering angle $2\theta$, the larger the studied structural dimension d may be.

Alternatively, according to Bragg's law, the evaluation of scattered X-ray intensities in the larger angular region (WAXS) enables conclusions concerning the small atomic crystalline structures of materials.

In the area of nanomaterials, structural changes have simultaneous effects in both regions; it is therefore desirable to be able to study both scattering regions simultaneously.

In the case of radiation through the sample, measurements must be made at very small scattering angles which are as close as possible to the incident beam.

Figure 1:
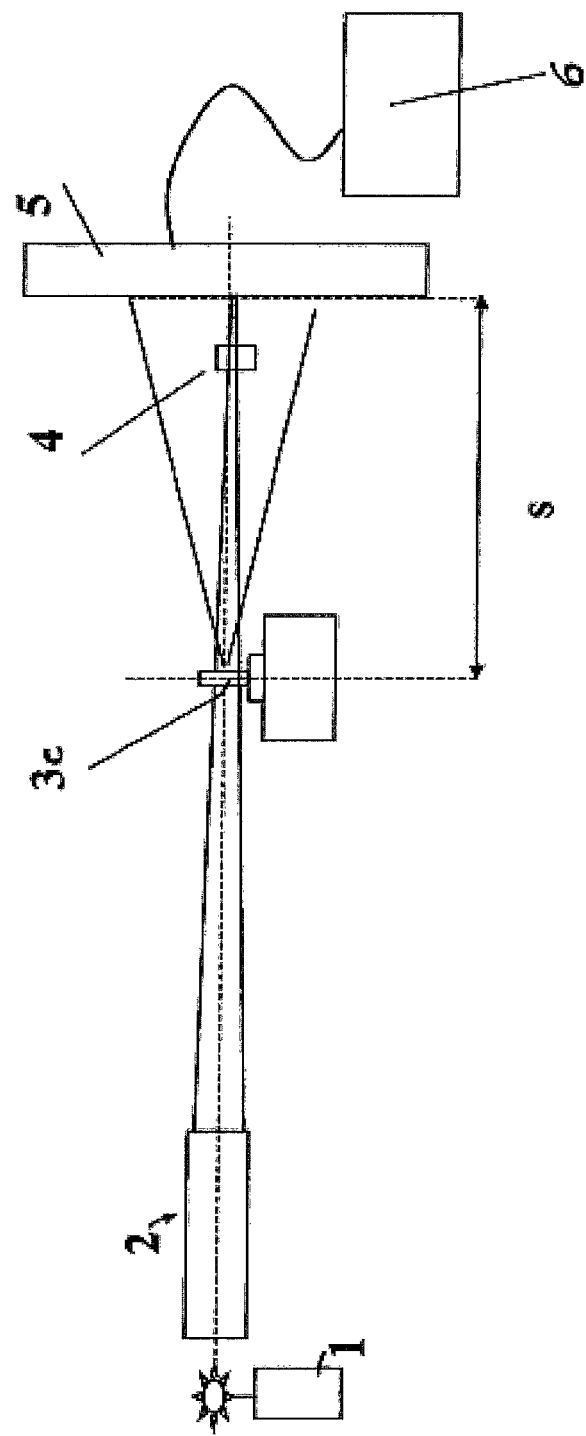
FIG. 1 shows a known basic structure for a measuring apparatus for small-angle scattering measurements.

The X-ray beam emitted from an arbitrary X-ray source 1, e.g. a synchrotron, an X-ray tube, or a rotating anode, is formed by a subsequent X-ray optical system 2, which comprises various arrangements of collimation blocks and/or mirrors and other optical elements. In general, line and/or point-focussed convergent and/or parallel monochromatic beams are used. The corrections which are used for the given scattering geometries in order to correct the actual deviations from the ideal scattering experiment are known in the state of the art.

The tailored beam strikes the sample 3c and the scattered intensities are detected spatially resolved, using a suitable detector 5. According to the state of the art, one-dimensional detectors, e.g. a photodiode array, which detect the intensity distribution in a line perpendicular to the primary beam, are also known, as are 2-dimensional detectors, such as e.g. 2-dimensional photodiode arrays, CCD cameras, or image plates (IPs).

Limiting factors, beside the type of the X-ray optics 2 used for conditioning the beam prior to the irradiation of the sample, include the resolution of the detector, particularly limited by the pixel size and by crosstalk between the detector pixels, the correct sample-to-detector distance, and the possibility that the un-scattered primary beam can be shielded by means of a beamstop 4 in front of the detector 5.

Restrictive beam conditioning leads to diminished intensities, and hence long recording times and strong noise in the signal.

The minimum angle of resolution depends on the dimension of the incident beam and the spatial resolution of the detector employed. Accordingly, in order to be able to register evaluable scattering patterns, measurement devices in the meter range are often employed. Since the beam travels through relative long paths outside the sample, the measurement chambers must always be evacuated, in order to eliminate the background scattering of the air.

In the case of a large distance between the sample and the detector, the scattered intensity at the detector is decreased. This can be avoided by positioning the sample closer to the detector. Due to geometric reasons, at the same time a larger scattering-angle range can be covered.

DE 10 2006 029 449 B3 describes an apparatus of the general underlying type wherein it is possible to change the distance between the sample and the detector by means of a movable detector and metal bellows segments under vacuum, for guiding the beam. This membrane bellows apparatus with directly connected detector allows continuously changeable sample-to-detector distances and allows measurements up to $\theta=40°$. The handling and the space requirements for such a system make it impossible to use it for rapid, simple, and thorough characterisation of a sample. In such systems, the incoming beam is generally guided as a parallel beam.

N. Yagi, "Simultaneous record of the SAXS/WAXS pattern which uses Shad-o-Box which added change", [online, URL: http://www.ads-img.co.jp/products/rad-icon/pdf/saxswax-s.pdf, November 20119], illustrates simultaneous measurement of SAXS and WAXS with the aid of two fixed detectors which are adjusted to the intensity and resolution requirements of the angular ranges. The measurement of the intensity in the WAXS range occurs via fluorescence conversion into visible light. According to Rigaku, JP 2009-002805, the measurement of two angular ranges is achieved by two stationary detectors.

According to AT392160B, a slit- or point-collimated beam is produced without parasitic reflections, which allows an extremely compact setup with high intensities at all scattering angles. This allows a compact design with a sample-to-detector distance on the order of <10 cm to 30 cm. This apparatus, equipped with a suitable detector, a so-called "imaging plate", which is cylindrically symmetrically arranged around the sample which is arranged in the centre of the cylinder, allows measurement of very small scattering-angles up to angles greater than 40°.

This continuous measurement of the small-angle and large-angle ranges is carried out with the aid of X-ray imaging plates which can be digitalised and read by a special method, in an external apparatus. The resolution achieved is substantially determined by the reading process, but in general the imaging plates have the disadvantage of offline digitalisation of the scattering image. The possibility of arranging the imaging plates in a cylindrically symmetric manner plays a large role in the measurement accuracy, because with the small sample-to-detector distances employed in the SAXSess System, the distortion due to a planar detector surface in the wide-angle range, e.g. in the case of CCDs, plays a greater role. The resolution of such image plates is limited. Due to the low intensities at larger scattering angles, the interference structures at small angles appear relatively intensive, whilst at large scattering-angles the scattering intensities are low. In order to measure large scattering-angle ranges, one must use extremely long IPs or a combination of a plurality of diode arrays into a polyhedral configuration. With cylindrically symmetric IP or photodiode array detectors, scattering angles up to 80° are measurable.

Here it would be desirable to perform measurements with alternative, electrically readable detectors. However, these are not available with cylindrical symmetry and with sufficiently large detector surfaces. The use of flat detectors to measure simultaneously in the SAXS and WAXS range is limited by the necessary distance to the sample. The distance of the detector from the beam-forming unit, i.e. the source, mirror, and collimation block, is determined by the focus of the primary beam in the optical axis. Thus flat electronic detectors such as CCDs may be optionally set up in the small or large-angle region. The focus of the irradiated beam is in the detector plane, but a gap-free measurement is not achieved, and the rearrangement requires opening of the measurement chamber.

The described systems can generally be set up with a variety of sample holders and measurement cells, in order to be able to characterise a wide variety of samples. For SAXS measurement systems, for example, capillary holders for liquids, sample holders for solids, paste cells for viscous samples, and flow cells for automatic measurements and characterisation of reactions of liquid samples are also available, as well as a so-called VarioStage for positioning and orienting of solid samples. This sample holder facilitates rotational movements, tilting movements, and scanning movements of the sample in the beam, in order to carry out spatially resolved studies. A humidity cell for powder and film samples in a climate-controlled chamber has also been made available, as has an Autosampler for automatic filling of the capillary holder using a sliding rail system. In all these cases, the measurement position is approximately the same, in relation to the incoming beam. Movements of the sample with the sample holder vertically to the sliding rail system serve only for adjustment and minor variation of the measurement region on the sample.

Since the chip arrays for the electronic detectors are flat plates, and an array of multiple similar detectors is too expensive and cumbersome for standard applications in industry, it is not a simple matter to replace the imaging plates by compact electronic detectors. Additionally, one faces the problem that each detector has its own characteristic, and the necessary corrections and standardisations do not lead to a consistently evaluable image.

The object of the present invention was to build an apparatus of the initially described type which can be used for making measurements with detectors of any type, including those known from the state of the art, both in the small-angle measurement region and in the wide-angle and large-angle measurement region. The desired region covered should be from 0° to greater than 40°, and should provide overlapping scattering images in the momentum transfer region of 0-28/nm. Furthermore, larger scattering-angle ranges with smallest-area and only slightly curved IP- or photodiode array detectors up to 80° should be possible. In this, it is assumed that the small-angle region is 0-10°, and the large-angle region is ca. 10-50° or 80°, with slightly curved detector surfaces.

This problem is solved according to the invention with a method of the type described initially supra, having the features described in the predicate of claim 1. This enables, with only simple changes in the distance between the sample and the detector, alternate measurements of the small-angle scattering region and the large-angle scattering region, in the course of the measurements, without major refitting difficulties. In the process, the characteristic of the detector remains unchanged, and therefore the measurement results from the two scattering-angle regions can be readily evaluated and combined. The position of the detector with respect to the X-ray beam is not changed. It is basically simpler to displace the sample along the X-ray beam than to move a substantially more massive detector which is much more complex to adjust. Furthermore it is possible to move the sample along the X-ray beam in a very exact manner, whilst such a movement of a detector is accompanied by substantial decrease of measurement accuracy. Apart from that, it takes far more time to refit the detector than to move a sample, and thus measurements where a rapid sequence of measurements in the small-angle scattering region and in the large-angle scattering region is necessary are not possible.

According to the invention it is possible to move the sample with the sample remaining in the X-ray beam and in the optical axis of the device, with the sample being brought to another distance from the detector by means of the moving device. At the same time, the vacuum in the chamber is preserved. Adjustments are at the most made for image processing and scaling, and one obtains a consistent scattering image without having to readjust the measurement beam and the detector.

If, in the case of a predetermined distance between the X-ray beam source or the starting point of the X-ray beam directed onto the sample and the detector, for a predetermined number of sequential measurements, the distance between the sample and the detector can be changed and can be adjusted to a predetermined different value, it is possible for specific studies to predetermine the desired distances which the sample will be moved to for carrying out the desired scattering angle measurements.

It is possible that, in order to change the distance, it will be necessary to carry out a continuous movement of the sample in or opposite to the direction of the X-ray beam into the predetermined measurement position, or that the sample will be moved into at least two sample receivers which are positioned at different distances from the detector along the X-ray beam. Under the first possibility, the sample will be mounted on a movable device which will move the sample along the X-ray beam in a continuous rapid movement between the two predetermined distances from the detector. It is also possible for the sample to be moved from one sample receiver to a second sample receiver, manually or using a gripping device; these sample receivers will each be arranged at a defined predetermined distance from the detector.

The inventive method is particularly simple if it is provided that the beam geometry and measurement geometry are kept unchanged when the sample is moved, and/or during the movement of the sample these geometries remain unchanged in their position on or with respect to the axis of the X-ray beam. This makes it unnecessary to change the measurement system; the sample is merely moved from one position into another position, with the two positions having known, predetermined distances from the detector. In both positions, the sample is subjected to the X-ray beam in a predetermined manner, and provides a scattering pattern on the detector.

It may be provided that at a test position of the sample arranged close to the detector an X-ray scattering pattern is delivered to the detector for large angle scattering, and at a test position of the sample arranged far from the detector an X-ray scattering pattern is delivered to the detector for small-angle scattering. In the position of the sample at which the large-angle scattering region is delivered to the detector, it may also be provided that the small-angle scattering is shielded, if it is found that there is an unfavourable influence on the image from small-angle scattering when images are recorded over a longer period.

The inventive method is particularly suitable for recording of scattered X-ray beams with a plate-shaped CCD sensor. Such CCD sensors are costly, cumbersome, and time-consuming to adjust, and movement of such a sensor along the axis of the X-ray beam or the optical axis of the measurement device is costly, cumbersome, and time-consuming.

This apparatus enables rapid changing of the sample for recording of small-angle scattering and large-angle scattering, and the apparatus has a simple construction.

Figure 2:
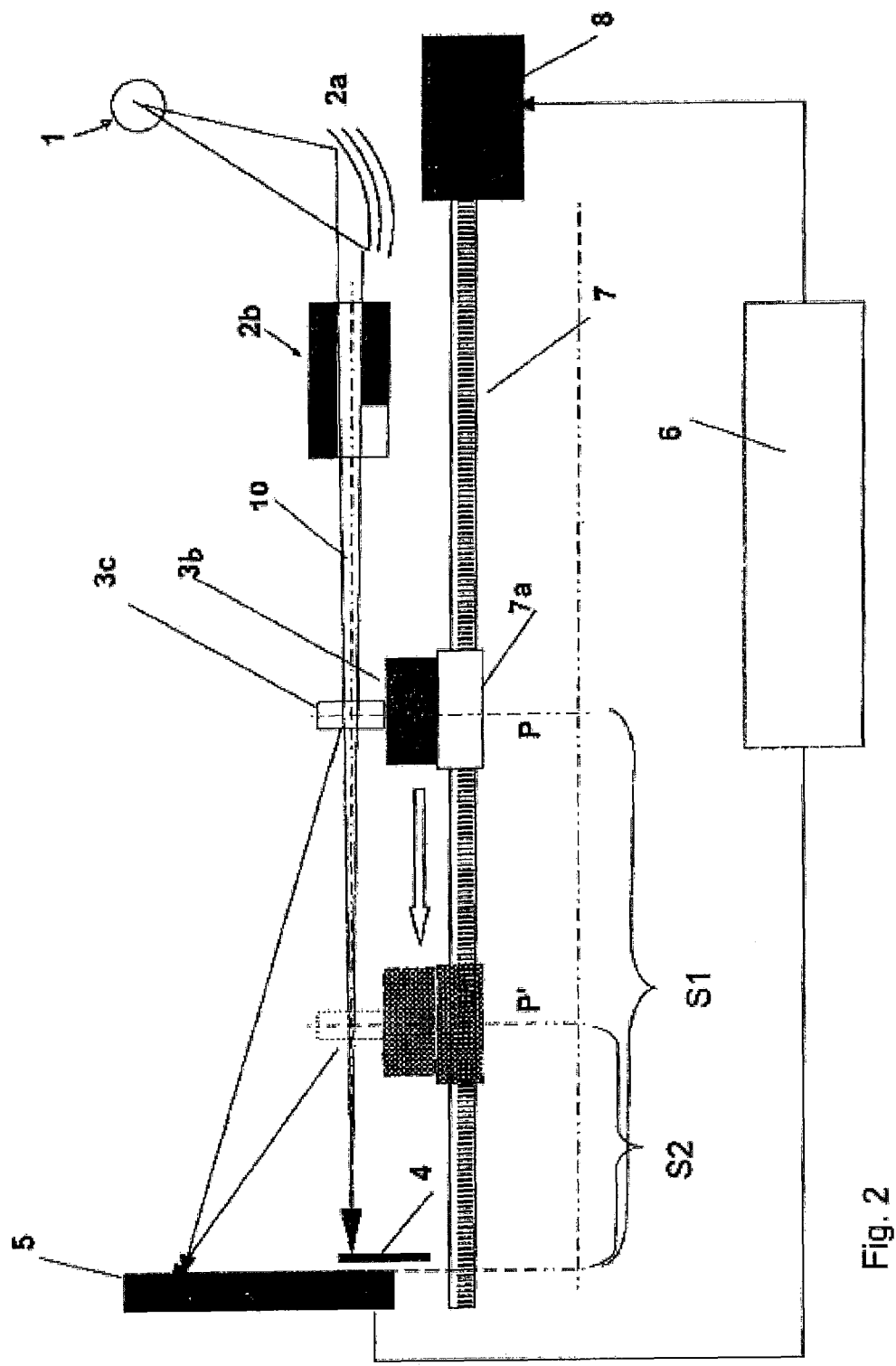
FIG. 2 shows a construction of an apparatus according to the invention.
Figure 3:
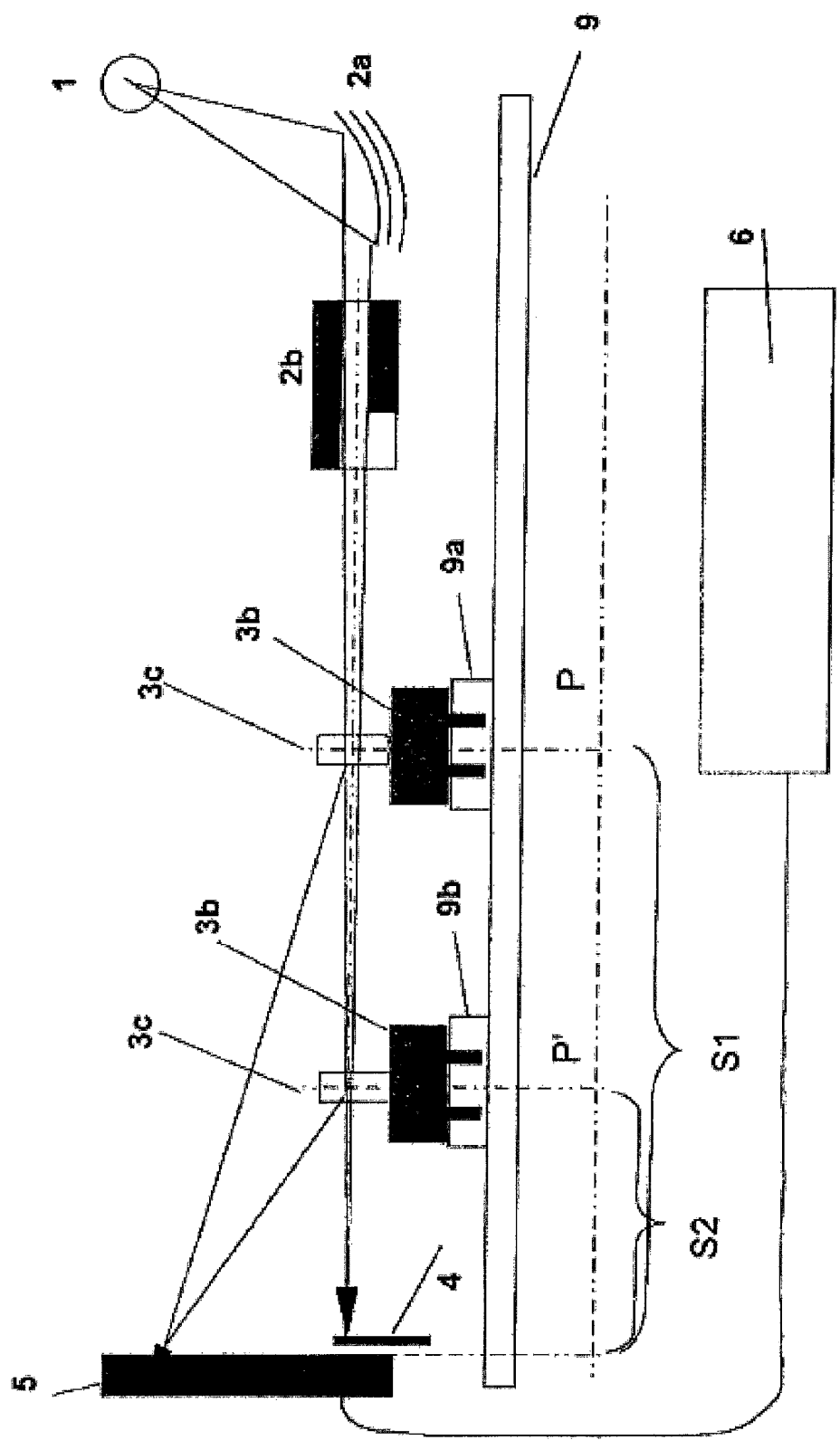
FIG. 3 shows an embodiment of an apparatus according to the invention.

The invention will be described in more detail below with reference to the drawings. FIG. 2 is a schematic representation of the construction of an apparatus in which the sample can be moved along the X-ray beam. FIG. 3 illustrates an embodiment of an apparatus wherein the sample can be moved along the X-ray beam into various predetermined recording positions.

FIG. 2 is a schematic representation of an inventive apparatus for study of the X-ray properties of a sample $3c$ which is positioned on a sample holder $3b$. The X-ray beam leaving an X-ray source 1 is focussed by an X-ray mirror $2a$ onto the plane of a detector 5. The width of the beam is established with a collimation block $2b$. Obviously it is also possible that a parallel X-ray beam or other X-ray beam geometries may be employed. Also, formation of a point focus or a line focus is possible. The mirror $2a$ and the collimation block $2b$ are adjustable with respect to the X-ray source 1 and the detector 5, wherewith the X-ray beam 10 can be guided independently of the sample position. The position of the sample $3c$ can be changed along the X-ray beam 10, with respect to the detector 5. This involves movement of the sample support $7a$ which bears the sample holder $3b$, relative to the X-ray beam 10 along the optical axis of the apparatus. The sample $3c$ is fixed to a sample holder $3b$, which may be releasably connected to a spindle nut which forms the sample support $7a$, which support can be moved along the X-ray beam 10 by means of a stepping motor which drives a screw spindle 7 which is capable of moving the spindle nut. In this way, the sample $3c$ is continuously movable along the optical axis and the X-ray beam 10. Position measurement can be accomplished, e.g., via a defined starting position and a counting of the revolutions of the spindle in the clockwise or counter clockwise direction, and multiplication times the pitch. Also for determination of the position, measurement devices may be provided which determine the distance between the detector 5 and the sample $3c$; these may comprise, e.g., potentiometers, incremental path recorders, inductive path recorders, measuring gauges, etc. Similarly, the distance between the spindle nut and a predetermined reference position can be measured. In particular, reference is made to the determination of the distance between the sample $3c$ and the detector 5 in the detector plane.

It is possible to use other displacing devices instead of a spindle. E.g., mechanical linear advancing devices may be provided parallel to the optical axis, with the sample being moved via linear motors or a rack and pinion drive.

As soon as the stepping motor moves the spindle 7, the spindle nut is moved along the X-ray beam 10 and the sample $3c$ is moved along the optical axis of the apparatus toward or away from the detector 5. The distance S1 shown in FIG. 2 between the sample $3c$ and the detector 5 corresponds to a relatively large distance, and the position P corresponds in practice to the distance for imaging in the small-angle scattering region. The distance S2 at which the sample $3c$ is arranged in position P' corresponds to the large-angle scattering region, wherein for reasons of the intensity the middle-angle and/or small-angle scattering region may be blocked by a shield 4.

It is also possible to make recordings during the movement of the sample $3c$, with continuous changing of the recorded scattering-angle pattern based on the changing distance of the sample $3c$ from the detector 5. The movement of the sample $3c$ is controlled by a control unit 6 which can also be utilised to carry out the evaluation of the detector signals. Thus the values of the distances are recorded along with the scattering measurement values determined by the detector 5.

Advantageously the distances for the measurements of the two scattering-angle regions are determined prior to making the measurements themselves. It is also possible to determine partial regions of the two scattering-angle regions, and to not collect images on the detector 5 for too small and too large limiting regions of the scattering and the respective regions.

An alternative procedure is illustrated in FIG. 3. Here, defined measurement positions P and P' are provided via sample receivers $9a$ and $9b$, bearing sample supports $3b$ with samples $3c$. The measurement positions P and P' are at distances S1 and S2 from the detector 5 and the detector plane respectively. Thus an exactly reproducible movement of the samples $3c$ with regard to the detector 5 is possible. On the receivers $9a$ and $9b$ exactly established guide means for the sample supports $3b$ can be provided which ensure exact positioning of the sample $3c$ in relation to the detector 5.

It is also possible to carry out the movement of the sample supports $3b$ by means of an automatically functioning device, e.g. a robot, and to provide recognition systems which recognise the positioning of the sample 3c in position P or P'.

Further, adapters may be provided on the sample receivers 9a and 9b, which adapters may accommodate different sample supports 3b. It is also possible for the sample supports 3b to be in the form of flow cells or cells with controlled atmospheres. In principle, the form of the sample supports is arbitrary.

There is no limitation connected with the possibility of placing the sample at different distances from the detector 5. Rather, it is possible that the measurement positions P and P' can be automatically positioned via the control unit 6. This allows the sample to be moved without breaking the vacuum.

Using the detector 5 as provided for, different angular regions can be subjected to measurements in immediately sequential measurements, without the need to recalibrate the detector, because the only change is in the distance between the sample 3c and the detector 5.

The advantages afforded by the inventive apparatus are independent of whether a focussed X-ray beam 10 or a parallel X-ray beam 10 is used.

The invention claimed is:

1. A method of studying the X-ray properties of samples (3c), wherein X-ray beams scattered at a sample (3c) are recorded by a detector (5) positioned at a distance from the sample (3c), and are evaluated with regard to the sample characteristics; characterized in that at a predetermined distance between the X-ray source (1) and the detector (5) or between the starting point (2b) of the X-ray beam (10) directed at the sample (3c) and the detector (5), for a predetermined number of successive measurements the distance (S1, S2) between the sample (3c) and the detector (5) is changed and is set at a predetermined different values.

2. A method according to claim 1, characterized in that the distance (S1, S2) is set to a value for which the small-angle scattering region and/or the large-angle or wide-angle scattering region is imaged on the detector (5).

3. A method according to claim 1, characterized in that, in order to change the distance, the sample (3c) is continuously moved in or opposite to the direction of the X-ray beam (10), into the predetermined measurement position (P, P').

4. A method according to claim 1, characterized in that the sample (3c) is moved in with the sample being mounted in at least two sample receivers (9b) positioned along the X-ray beam (10) at different distances (S1, S2) from the detector (5).

5. A method according to claim 1, characterized in that the beam geometry and measurement geometry are maintained unchanged during the movement of the sample (3c), and/or during the movement of the sample (3c) these geometries are maintained fixed in their position on or with respect to the axis of the X-ray beam (10).

6. A method according to claim 1, characterized in that the X-ray beams scattered at large-angle scattering are imaged on the detector (5) at a position (P') of the sample (3c) close to the detector, and the X-ray beams scattered at small-angle scattering are imaged on the detector (5) at a position (P) of the sample (3c) distant from the detector.

7. A method according to claim 1, characterized in that the scattered X-ray beams are recorded with a plate-shaped CCD sensor (5) or a curved imaging plate or a diode detector.

8. A method according to claim 1, characterized in that the distance between the X-ray beam source (1) or the starting point (2b) of the X-ray beam (10) directed onto the sample (3c) and the detector (5) is maintained unchanged during the measurement.

9. An apparatus for studying the X-ray properties of samples (3c), having an X-ray beam source (1), a sample support (3b) for holding the sample (3c), and a detector (5), which detector is positioned at a fixed distance from the X-ray beam source (1) or from a starting point or an X-ray optics (2) respectively of the X-ray beam (10) directed onto the sample (3c), wherein the X-ray beams scattered by the sample (3c) are recorded by the detector (5) positioned at a distance (S1, S2) to the sample (3c), and signals are evaluated with regard to the characteristics of the sample; characterized in that:

a positioning unit (8) is provided by means of which the sample (3c) is moveable parallel to the axis of the X-ray beam (10) into a testing position (P') close to the detector (5) in which an image is produced on the detector (5) in a large-angle scattering region and is produceable also in a small-angle scattering region, and into a testing position (P) distant from the detector in which an image is produced on the detector (5) in the small-angle scattering region; or along the axis of the X-ray beam (10) at least two mutually separated positions (P, P'), receivers (9a, 9b) for the sample (3c) are positioned, wherein the position of the sample (3c) in the receiver (9b) which is close to the detector results in production of an image in the large-angle scattering region on the detector (5) and is producible also in the small-angle scattering region, and the position of the sample (3c) in the receiver (9a) which is distant from the detector results in production of an image in the small-angle scattering region on the detector (5).

10. An apparatus according to claim 9, characterized in that the positioning unit (8) has a sample support (7a) movably mounted on a spindle (7), which spindle (7) is rotatable by an adjusting motor or stepping motor, wherein the sample support (7a) is movable along the axis of the X-ray beam (10).

11. An apparatus according to claim 9, characterized in that the detector (5) is a CCD sensor, IP sensor, or diode array sensor.

* * * * *